United States Patent
Togawa

(10) Patent No.: US 6,970,243 B2
(45) Date of Patent: Nov. 29, 2005

(54) PARTICLE SIZE DISTRIBUTION MEASURING APPARATUS

(75) Inventor: Yoshiaki Togawa, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 10/077,616

(22) Filed: Feb. 15, 2002

(65) Prior Publication Data

US 2002/0113964 A1   Aug. 22, 2002

(30) Foreign Application Priority Data

Feb. 19, 2001   (JP) ............................ 2001-042383

(51) Int. Cl.$^7$ ........................................... G01N 15/02
(52) U.S. Cl. ..................................... 356/336; 356/343
(58) Field of Search ................................ 356/335–343; 250/574, 575, 573, 222.2

(56) References Cited

U.S. PATENT DOCUMENTS

| 4,243,318 | A | * | 1/1981 | Stohr ........................... 356/39 |
| 4,341,471 | A | * | 7/1982 | Hogg et al. .................. 356/343 |
| 4,762,413 | A |   | 8/1988 | Namba et al. |
| 4,781,460 | A |   | 11/1988 | Bott |
| 4,828,388 | A |   | 5/1989 | Namba |
| 4,957,363 | A | * | 9/1990 | Takeda et al. ................. 356/73 |
| 4,999,513 | A | * | 3/1991 | Ito et al. ...................... 250/575 |
| 5,007,737 | A | * | 4/1991 | Hirleman, Jr. ............... 356/336 |
| 5,105,093 | A | * | 4/1992 | Niwa ........................... 250/574 |
| 5,164,787 | A | * | 11/1992 | Igushi et al. ................. 356/336 |
| 5,185,641 | A | * | 2/1993 | Igushi et al. ................. 356/336 |
| 5,379,113 | A | * | 1/1995 | Niwa ........................... 356/336 |
| 5,471,298 | A |   | 11/1995 | Moriya |
| 5,684,583 | A |   | 11/1997 | Abe et al. |
| 5,760,900 | A | * | 6/1998 | Ito et al. ...................... 356/338 |
| 5,796,480 | A | * | 8/1998 | Igushi ......................... 356/336 |
| 5,956,139 | A |   | 9/1999 | Meyer et al. |
| 6,091,492 | A |   | 7/2000 | Strickland et al. |
| 6,177,994 | B1 | * | 1/2001 | Watson et al. ............... 356/343 |
| 6,473,177 | B2 |   | 10/2002 | Yamaguchi |
| 6,473,178 | B2 | * | 10/2002 | Shimaoka .................... 356/336 |

FOREIGN PATENT DOCUMENTS

| JP | 59-160741 | 9/1984 |
| JP | 61-178643 | 8/1986 |
| JP | 05-113396 | 5/1993 |
| JP | 2001-33376 | 2/2001 |

* cited by examiner

Primary Examiner—Hoa Q. Pham
(74) Attorney, Agent, or Firm—Brown Raysman Millstein Felder & Steiner LLP

(57) ABSTRACT

A particle size distribution measuring apparatus which can enhance the precision and the reliability of measurements by eliminating the region of the particle size having inferior measuring precision and resolution is disclosed.

In one embodiment, the particle size distribution measuring apparatus has a cell for receiving particles, a light source section for irradiating laser lights with a plurality of wavelengths to the cell, a detector for measuring the intensity of a direct light passing through the cell and the scattered lights at a plurality of scattering angles, and an arithmetic processing section which determines the particle size distribution by using the laser light of one wavelengths for the region of the particle size having low sensitivity at another wavelength in the whole range of the particle size to be measured to compensate the sensitivity of the region.

9 Claims, 5 Drawing Sheets

PARTICLE SIZE DISTRIBUTION MEASURING APPARATUS

FIELD OF THE INVENTION

The present invention relates to a particle size distribution measuring apparatus, and more particularly to a laser diffraction/scattering particle size distribution measuring apparatus.

BACKGROUND OF THE INVENTION

Conventionally, a laser diffraction/scattering particle size distribution measuring apparatus obtains a particle size by detecting the intensity of light scattered by a particle with a sample cell being irradiated with a laser and detected by a ring detector (and other photodetector). Thereafter, the detected scattered light intensity is converted to a particle size distribution by arithmetic processing.

FIG. 7 shows a schematic of a typical optical system in a conventional a laser diffraction/scattering particle size distribution measuring apparatus 10. As shown in FIG. 7, the typical optical system in a conventional laser diffraction/scattering particle size distribution measuring apparatus 10 comprises a laser light source 11 which emits laser light L, a lens 12 for condensing the laser light L from the laser light source 11, a cell 13 for receiving a sample, and a plurality of detectors $D_0$, $D_1$, $D_2$ and so forth comprising the ring detector. The laser light source may emit laser light L at a wavelength such as 633 nm.

The plurality of detectors D0, D1, D2 and so forth formed on the foregoing ring detector detect the intensity of scattered light at various scattering angles corresponding to the plurality of detectors D0, D1, D2. The plurality of detectors D0, D1, D2 may also arranged outside the ring detector. The plurality of detectors D0, D1, D2 are contrived so as to maintain the particle size detecting sensitivity and are capable of measuring the intensity of scattered light at a wide range of scattering angles ranging from minute scattering angles to a wide scattering angles with the respective detectors corresponding to the various scattering angles through the use of a plurality of detectors D0, D1, D2 and so forth including detectors positioned outside the ring detector.

There is a region of the particle size having high sensitivity which is specific to the respective detectors, in each of a great number of detectors D0, D1, D2 and so forth, are arranged as described above. Accordingly, the determination of the particle size distribution at high sensitivity has been carried out through arithmetic processing, which requires measuring the scattering lights Ls of many scattering angles using a great number of detectors D0, D1, D2 and so forth.

In a conventional particle size distribution measuring apparatus, the region of the particle size at which the sensitivity of the scattering lights Ls becomes too weak for any scattering angle is dependent on the wavelength of the laser light L used to irradiate a particle and the refractive index of the particle. As a result, the detecting sensitivity is inevitably reduced. FIG. 2 shows the detecting sensitivity of the respective detectors D0, D1, D2 and so forth relative to a particle size when the particle size distribution of a certain refractive index is determined using laser light L having a specific wavelength, such as 633 nm.

In FIG. 2, reference characters Ca1, Ca2 and so forth show the sensitivity curves of the detectors D0, D1, D2 and so forth, respectively. As illustrated in FIG. 2, it is found that the region of the particle size at which the sensitivity of the scattering light Ls becomes too weak for any scattering angle exists around the particle size of 2 m when using the laser light L of 633 nm to measure a sample. Incidentally, this tendency increases as the color of the particle becomes near white.

In response to the aforementioned shortcomings, when using a conventional the laser diffraction/scattering particle size distribution measuring apparatus, an effort has been made to obtain measurements which are not so poor, particularly in the region of the particle size at which the intensity of the scattering lights Ls is weak. This has been accomplished by developing a technique of deriving a particle size distribution by arithmetically processing the data of the intensity of the scattering light Ls obtained at the respective detectors. However, a decline in resolution could not be avoided in the region of the particle size at which the intensity of the scattering light Ls becomes too weak, when compared with the region of the particle size at which the intensity of the scattering light Ls was high.

The present invention has been made in view of such circumstances and an object of the present invention is to provide a particle size distribution measuring apparatus which can enhance the precision and the reliability of measurements by eliminating the region of the particle size having measuring precision and resolution inferior to another region. This is accomplished through elimination of the region of the particle size in which reduction in sensitivity arises.

SUMMARY OF THE INVENTION

To achieve the above object, the particle size distribution measuring apparatus according to the present invention is characterized by having a cell for receiving particles, a light source section for irradiating laser lights having a plurality of wavelengths to the cell, a detector for measuring the intensity of a direct light passing through the cell and scattering light at respective scattering angles, and an arithmetic processing section. The arithmetic processing section determines the particle size distribution by using the laser light of a different wavelength for the region of the particle size having low sensitivity than the wavelength in the whole range of the particle size to be measured, thereby compensating for the low sensitivity of the region.

Accordingly, when using the particle size distribution measuring apparatus of the present invention, the specific region of the particle size having low sensitivity is eliminated thereby resulting in the elimination of the region of the particle size having a measuring precision and resolution inferior to another region of the particle size. As a result, the precision and the reliability of measurements of a particle size distribution are enhanced.

When the foregoing light source section consists of a plurality of light sources irradiating the laser lights with respective different wavelengths, it is possible to make the wavelength of the irradiating laser light stable and to enhance analyzing precision correspondingly.

In case that the foregoing detector measures the intensity of the direct light and scattering lights having respective scattering angles commonly irrespective of the wavelength of the laser light and that the light source section irradiates the laser light changing the wavelength in sequence, it is possible to reduce the manufacturing cost of the particle size distribution measuring apparatus and to eliminate the measuring errors due to the difference between detecting sensitivity of the detectors themselves.

When a shutter which transmits only the laser light of the selected wavelength of the laser lights irradiated from the foregoing light source section and shuts off the laser light of another wavelength is provided, and the wavelength of the laser light to be irradiated becomes changeable through moving the shutter, it is possible to reduce a time of period for measuring and to enhance measuring precision since it becomes possible to quickly and precisely make selection of the wavelength of the laser light to be irradiated.

When the longest wavelength is at least 1.5 times larger than the shortest wavelength of the foregoing laser lights irradiated, it becomes to mutually compensate the regions at which the sensitivity is low by using the laser lights of the longest wavelength and the shortest wavelength and sufficient sensitivity may be attained in the whole region.

DETAILED DESCRIPTION OF THE PREFERRED EMBODIMENTS

Figure 1:
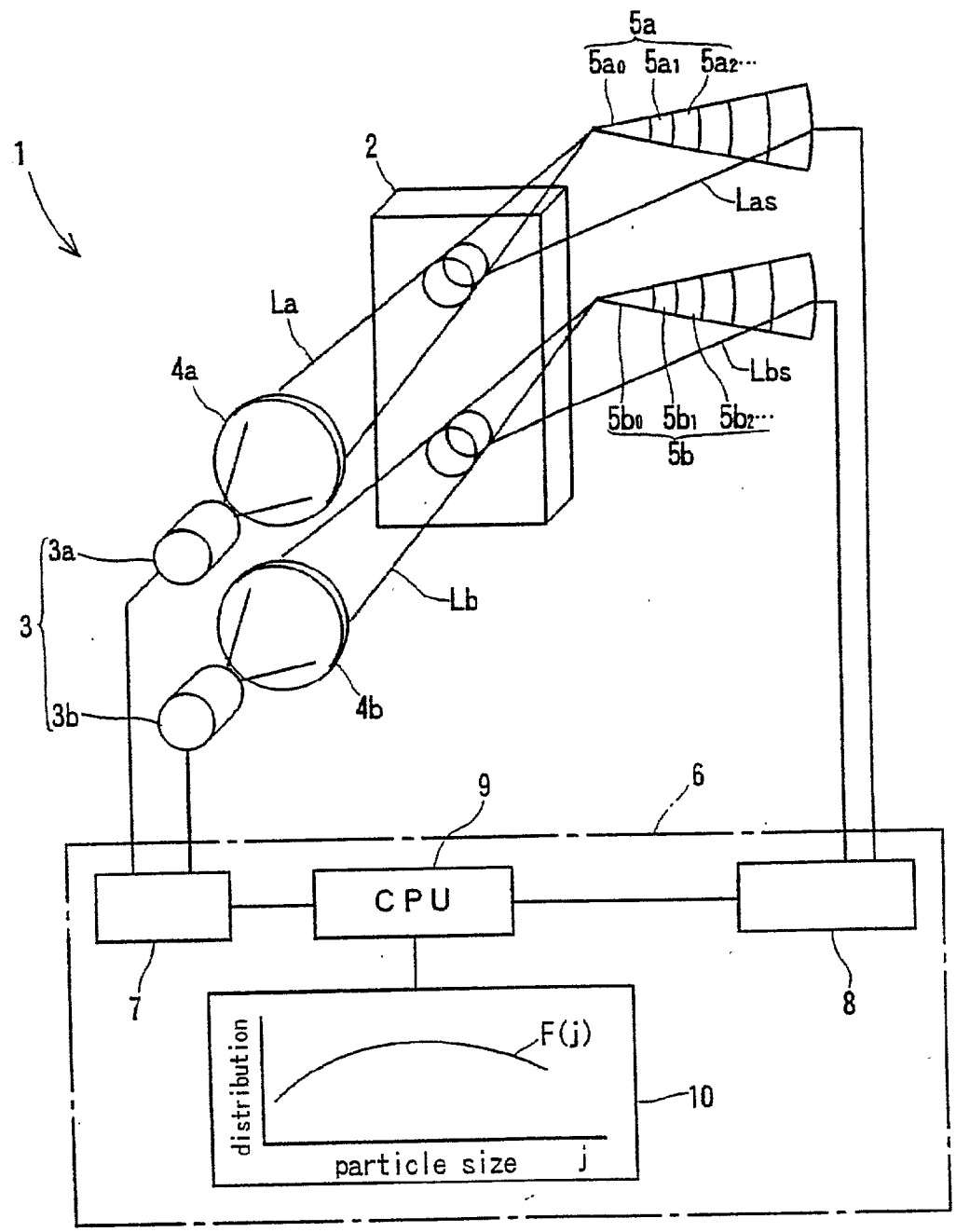
FIG. 1 shows schematically a construction of a particle size distribution measuring apparatus according to the present invention.

FIG. 1 shows an embodiment of a particle size distribution measuring apparatus 1 of the present invention which includes a sample cell 2 for receiving the sample to be measured, at least two laser light sources 3a, 3b capable of emitting laser lights $L_a$, $L_b$, at least two projection lenses 4a, 4b for receiving and condensing the laser light $L_a$, $L_b$ from the respective laser light sources 3a, 3b, and at least two ring detectors 5a, 5b for measuring the respective laser lights $L_a$, $L_b$ transmitted and scattered by the sample within the cell 2. Those skilled in the art will appreciate that the laser lights $L_a$, $L_b$ have mutually different wavelengths. In addition, the present embodiment includes at least two sets of optical systems for measuring the scattering light.

As illustrated in FIG. 1, the present embodiment of the foregoing particle size distribution measuring apparatus 1 may include a control section 6 which comprises a power unit 7 for supplying electric power to the foregoing light source 3a, 3b, an input interface 8 for inputting signals of measurements from the respective detectors 5a, 5b, an arithmetic processing section 9 capable of controlling the foregoing power unit 7 which drives the light sources 3a, 3b and inputting measurement signals received from the respective detectors 5a, 5b, and a display 10 for displaying the measurements derived by the arithmetic processing section 9.

The foregoing at least two laser light sources 3a, 3b comprise the light source section 3. In one embodiment, the light source 3a may comprise a Helium Neon laser irradiating laser light $L_a$ at a wavelength of about 633 nm, while the light source 3b may comprise a semiconductor laser diode irradiating the laser light $L_b$ at a wavelength of about 405 nm. Those skilled in the art will appreciate that a plurality of laser light sources or wavelengths may be used in the present invention and exemplary embodiment described above is not intended to limit the present invention.

The laser light $L_a$, $L_b$ emitted by the respective laser light sources 3a, 3b is condensed and focused by the projection lenses 4a, 4b onto the detectors 5a, 5b after passing through the sample cell 2. In the sample cell 2, the particles present within the sample are suspended or fixed, and the laser lights $L_{as}$, $L_{bs}$ scattered by the particles contained within the sample are detected by the detectors $5a_0$, $5a_1$, $5a_2$ and so forth, and by the detectors $5b_0$, $5b_1$, $5b_2$ and so forth. Additional detectors (not shown) may be arranged around the cell 2.

The detectors $5a_0$, $5a_1$, $5a_2$ and $5b_0$, $5b_1$, $5b_2$ which measure the intensity of the laser light $L_a$, $L_b$ passed through the cell 2 and are arranged at the center of the ring detectors 5a, 5b and aligned so that the center of the detectors $5a_0$, $5b_0$ is coincident with an optical axis of the laser light $L_a$, $L_b$. Further, the detecting channels $5a_1$, $5a_2$ and so forth, and $5b_1$, $5b_2$ and so forth, for the respective detectors 5a, 5b may have shapes which are coaxial with the center of the detectors $5a_0$, $5b_0$ and are may be radially divided into a plurality of parts.

Further, although not illustrated in FIG. 1, additional detectors may be installed separately for measuring the intensity of the laser light source 3a, 3b. The respective detectors $5a_0$, $5a_1$, $5a_2$ and so forth, and $5b_0$, $5b_1$, $5b_2$ and so forth, detect the intensity of the scattered light at a plurality of scattering angles, in addition to the scattered light by detectors (not shown) arranged outside the ring detector.

As described previously in FIG. 2, when using a single laser light $L_a$, the region of the particle size at which the sensitivity of the scattered light becomes too weak for any scattering angle (i.e. low-sensitivity region). The reference character Ha indicates a region of the particle size becoming too weak in the intensity of the scattered light, thereby resulting in a low-sensitivity region.

In the present invention, the high detecting sensitivity is consistently maintained for a wide range of particle sizes by using the light source section 3, which is capable of emitting the laser lights $L_a$, $L_b$ with a plurality of wavelengths, and with the detectors $5a_1$, $5a_2$ and so forth, and $5b_1$, $5b_2$ and so forth, which are capable of detecting the intensity of the scattered light at various scattering angles ranging from minute angle to a wide angle resulting from the respective laser lights $L_a$, $L_b$. A specific operation thereof is described below in reference to FIGS. 2 to 5.

Figure 2:
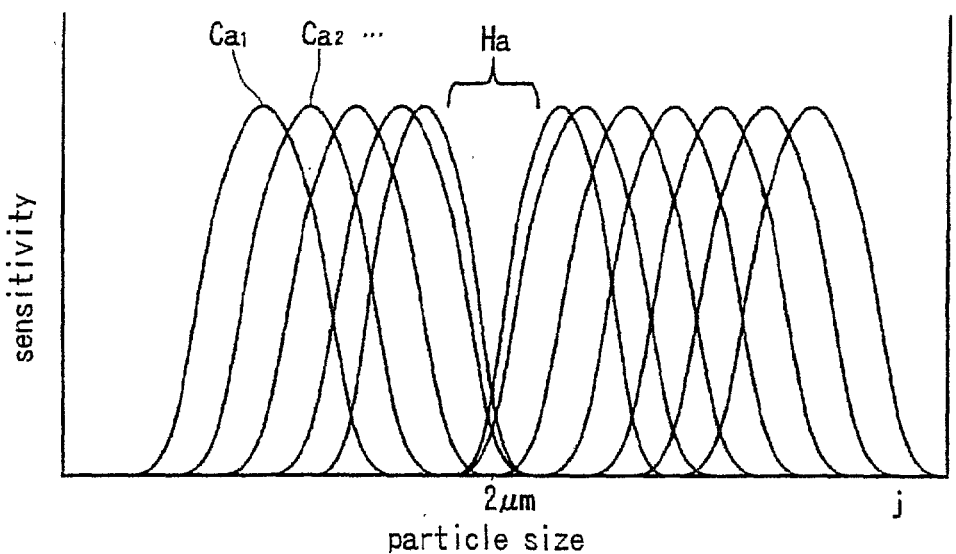
FIG. 2 shows the relationships between a particle size and sensitivity in using a laser light with one wavelength.

FIG. 2 shows the sensitivity curves $Ca_1$, $Ca_2$ of the respective detectors $5a_1$, $5a_2$. The low-sensitivity region Ha of the sensitivity curves $Ca_1$, $Ca_2$ depends on the refractive index resulting from the particle and the wavelength of the laser light $L_a$ used to irradiated to the particle. Therefore, it is possible to adjust the low-sensitivity region Ha by changing the wavelength of the laser light emitted from the light source 3a.

Figure 3:
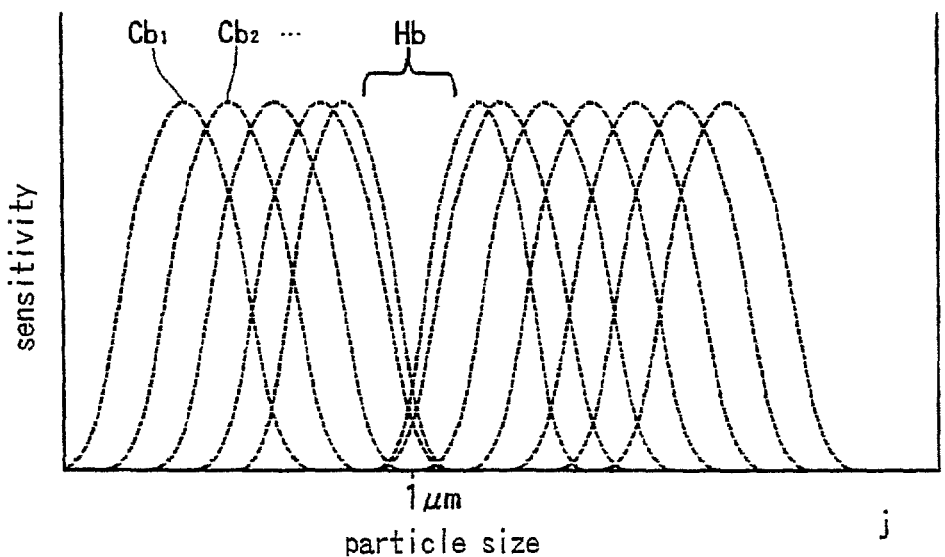
FIG. 3 shows the relationships between a particle size and sensitivity in using a laser light with another wavelength.

FIG. 3 shows the relationship between the particle size and the sensitivity when the laser light $L_b$ with a wavelength of 405 nm is used to irradiated the same sample as shown in FIG. 2. In FIG. 3, the sensitivity curves $Cb_1$, $Cb_2$ and so forth are shown for the respective detectors $5b_1$, $5b_2$ and so forth. The low-sensitivity region Hb of the sensitivity curves $Cb_1$, $Cb_2$ is shown. FIG. 3 shows the region of the particle size at which the scattered light detecting sensitivity of the respective detectors $5b_1$, $5b_2$ becomes low when using the laser light $L_b$ (i.e. the low-sensitivity region).

The arithmetic processing section 9 controls the power unit 7 which drives the light sources $3a$, $3b$. The light sources $3a$, $3b$ may be driven in a plurality of ways, including, for example, alternately driven. The arithmetic processing section 9 inputs the measurements of the intensity corresponding to the scattered lights detected by the detectors $5a$, $5b$, and determines the results in combination of the measurements corresponding to wavelengths from the laser lights $L_a$, $L_b$.

In an alternate embodiment, the light source section 3 may be provided with a laser shutter or shutoff plate positioned between the light sources $3a$ and/or $3b$, and the cell 2. The laser shutter or shutoff plate may permit the cell 2 to be irradiated with either laser light $L_a$ or $L_b$, or both, and may be freely selectable by driving the shutter or shutoff plate instead of the controlling of the power unit 7 by the arithmetic processing section 9.

Figure 4:
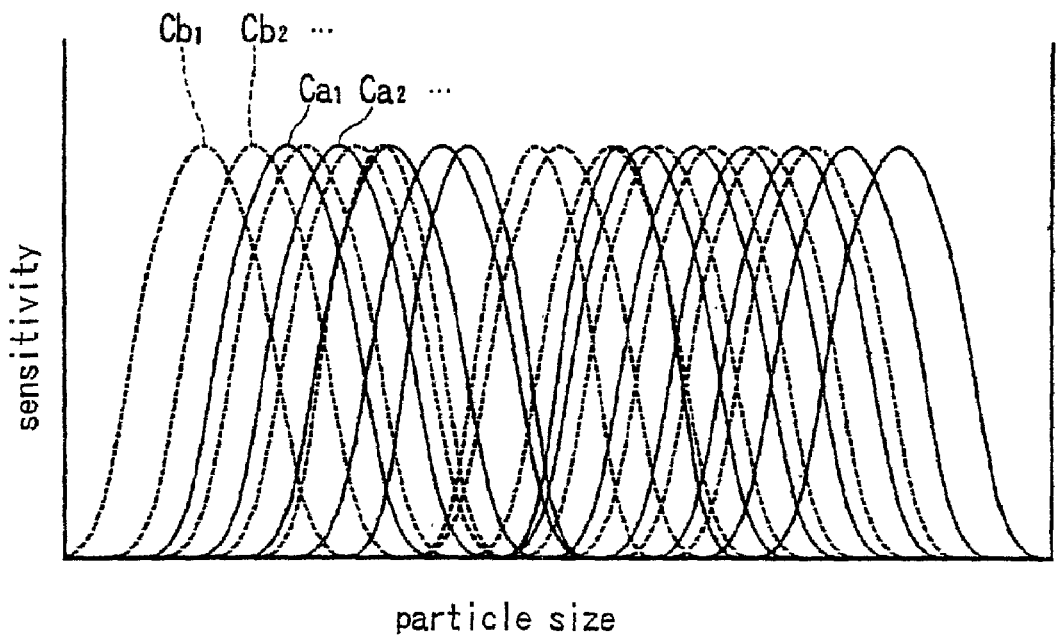
FIG. 4 shows the relationships between a particle size and sensitivity in using laser lights with both wavelengths.

FIG. 4 shows the detecting sensitivity of the combined measurements of the scattered lights $L_{as}$, $L_{bs}$ relative to the laser lights $L_a$, $L_b$ as measured by the respective detectors $5a_1$, $5a_2$ and so forth, and $5b_1$, $5b_2$ and so forth, in relation to the particle size. As FIG. 4 shows, the measuring process may be done at high-sensitivity for any particle size by using the laser lights $L_a$, $L_b$ having different wavelengths to measure the scattered light.

In this embodiment, since the wavelength of the laser light $L_a$ is about 633 nm and the wavelength of the laser light $L_b$ is about 405 nm, the wavelength of the laser light $L_a$ (the longer wavelength) is at least 1.5 times larger than the wavelength of the laser light $L_b$ (the shorter wavelength). Therefore, the low-sensitivity regions Ha, Hb of both laser lights $L_a$, $L_b$ do not overlap one another. That is, the specific region of a particle size of low-sensitivity may be eliminated across the entire measuring range by forming the detectors $5a$, $5b$ such that both optical systems mutually compensate for the low sensitivity regions Ha, Hb of the particle size. This may accomplished by appropriately selecting the wavelengths of the laser lights $L_a$, $L_b$ emitted from the light sources $3a$, $3b$, wherein the longest wavelength (laser light $L_a$) is at least 1.5 times larger than the shortest wavelength (laser light $L_b$) which is used to irradiate the sample.

Further, even though the longest wavelength (laser light $L_a$) is at most 1.5 times larger than the shortest wavelength (laser light $L_b$), and the foregoing low-sensitivity regions Ha, Hb somewhat overlap, the measuring sensitivity may be reliability enhanced over a measuring procedure using only the laser light $L_a$ or $L_b$ of the single wavelength, which is accomplished by combining the analyses of the laser lights $L_a$, $L_b$ of different wavelengths. In addition, the present invention does not limit the wavelengths of the respective laser light to be used in the arithmetic processing of the particle size distribution to the two systems. Moreover, those skilled in the art will appreciate that laser lights of two or more wavelengths may be used in combination.

Figure 5:
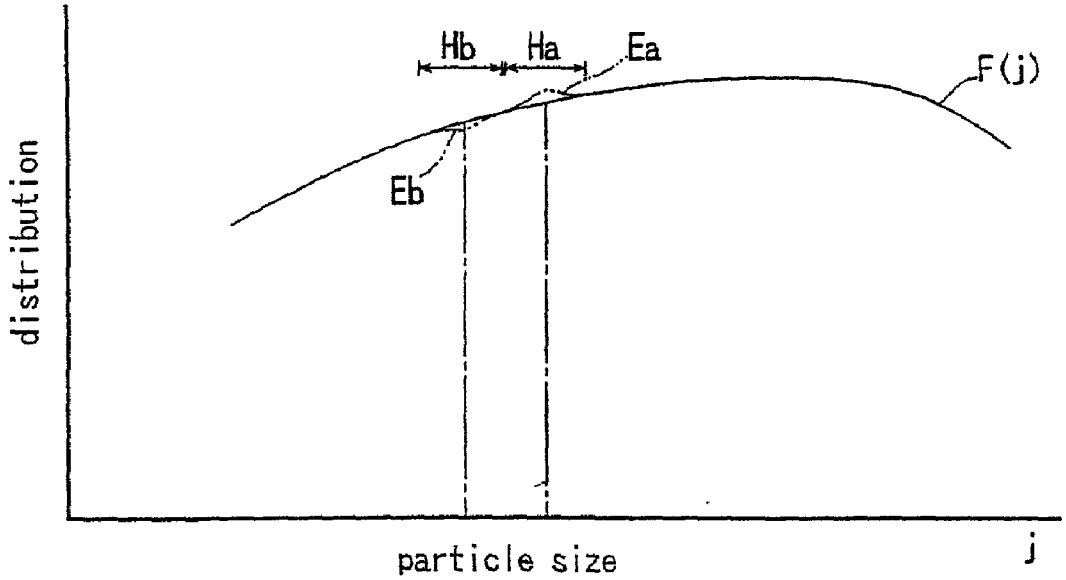
FIG. 5 shows an example of results of arithmetic processing of a particle size distribution.

FIG. 5 conceptually shows an example of the particle size distribution measured by the particle size distribution measuring apparatus 1 of the present invention. In FIG. 5, F(j) is a function of the particle size distribution which indicates the concentration of a particle size j, Ea represents an error resulting from the decline of the sensitivity, which can arise when the particle size distribution F(j) is determined by using only the laser light $L_a$, and Eb represents an error resulting from the decline of the sensitivity, which can arise when the particle size distribution F(j) is determined by using only the laser light $L_b$. That is, both errors Ea, Eb can become large in the range of the low-sensitivity regions Ha, Hb.

However, when the laser lights $L_a$, $L_b$ of a different wavelengths are used as shown in the present invention, the low-sensitivity regions Ha, Hb cancel each other to compensate the measuring sensitivity and therefore the foregoing arithmetic processing section 9 (referring to FIG. 1) can accurately determine the precise particle size distribution as illustrated by a solid line in FIG. 5.

In addition, the arithmetic processing may be performed more precisely since there are redundant measurements to be arithmetically processed when the arithmetic processing of the particle size distribution is performed. That is, the measuring precision of may be enhanced across the whole region of measurement. In addition, the aforementioned enhancement in measuring precision may also be achieved in regions other than the foregoing low-sensitivity regions Ha, Hb.

In the embodiment described above, the optical systems $3a$, $4a$, $5a$ used for determining the intensity of the scattered light by using the laser light $L_a$ are separate from the optical systems $3b$, $4b$, $5b$ determining the intensity of the scattering light by using the laser light $L_b$. Therefore, it is possible to drive both of the light sources $3a$, $3b$ and input the measurements from the respective detectors $5a_0$, $5a_1$, $5a_2$ and so forth, and $5b_0$, $5b_1$, $5b_2$ and so forth, simultaneously, provided the individual optical systems $3a$, $4a$, $5a$, and $3b$, $4b$, $5b$, can be adequately isolated form one another, thereby reducing the time required for measuring the particle size distribution.

In another embodiment, the respective optical systems $3a$, $4a$, $5a$, and $3b$, $4b$, $5b$, may share a common light source provided the light source is capable of emitting the laser light having a plurality of wavelengths as the light source section 3. In this case, it is possible to reduce the number of members composing the optical system, and the manufacturing cost correspondingly. That is, the optical systems in the particle size distribution measuring apparatus 1 of the present embodiment may be constructed identically or may be combined, except for the wavelengths of the laser light source.

Figure 6A:
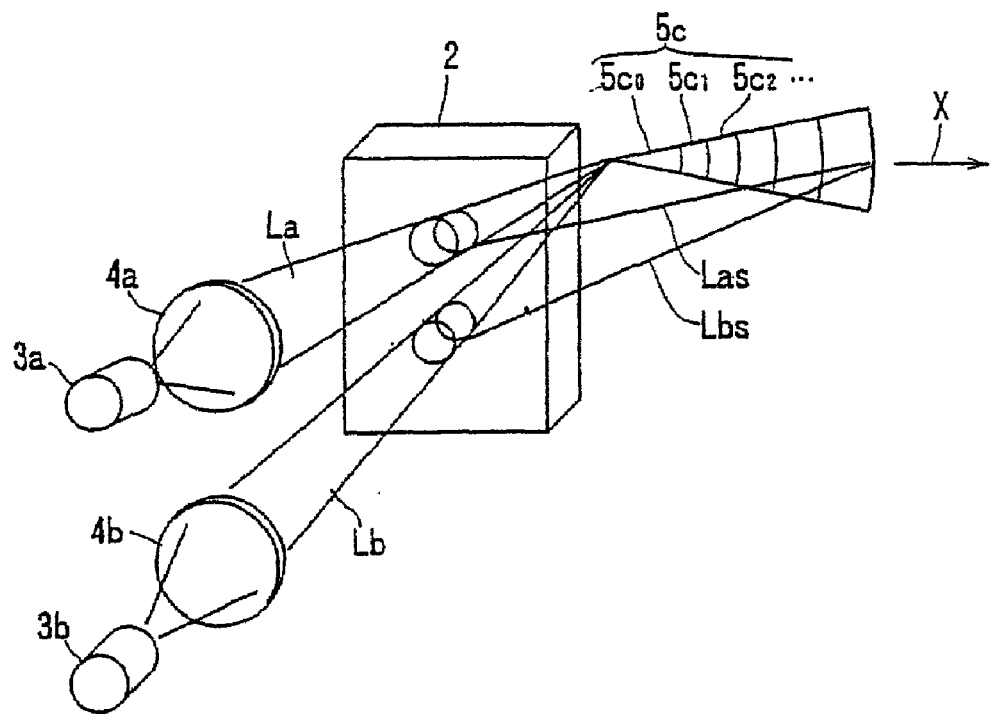
FIG. 6 shows another example of the particle size distribution measuring apparatus according to the present invention.
Figure 6B:
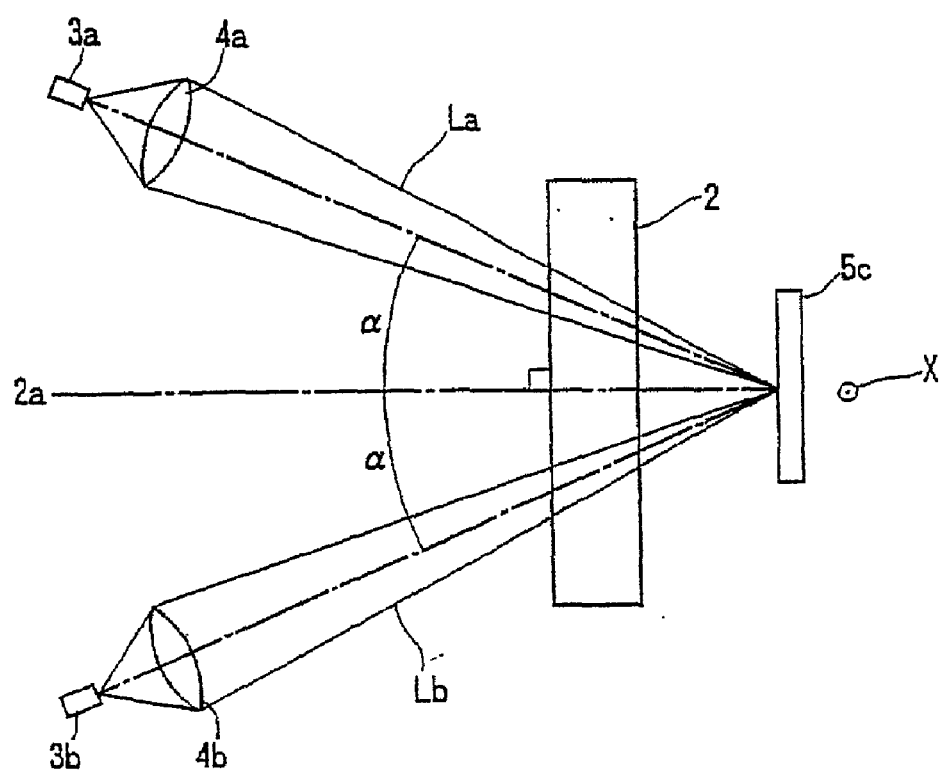
Figure 7:
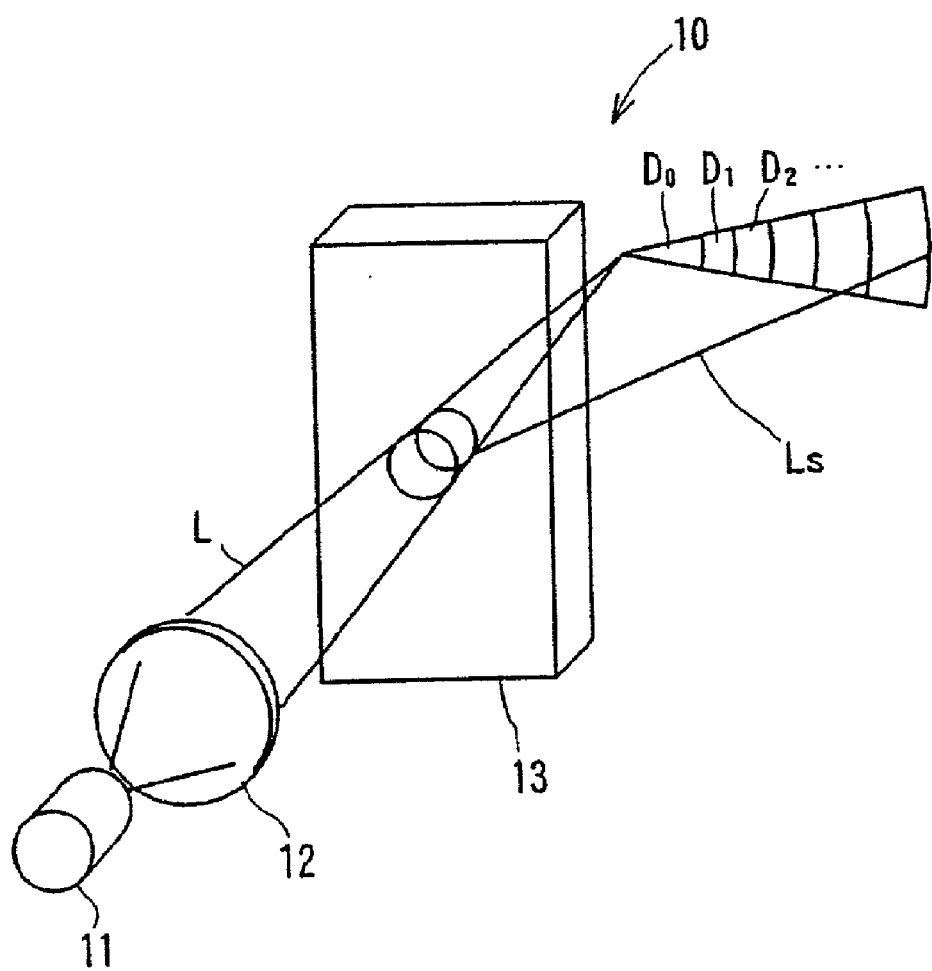
FIG. 7 shows an example of a conventional particle size distribution measuring apparatus.

FIGS. 6A–6B show another embodiment wherein one ring detector is shared between two sets of the optical systems $3a$, $4a$, and $3b$, $4b$. FIG. 6A provides a perspective view thereof and FIG. 6B provides a corresponding side view of the aforementioned embodiment. In FIGS. 6A–6B, similar reference characters to FIG. 1 designate similar or equivalent members. Those skilled in the art will appreciate that the present embodiment operates in a manner consistent with the previous embodiments.

In FIGS. 6A–6B, at least one detector or ring detector $5c$ is centrally positioned to be coincident with a focus position of the laser light $L_a$, $L_b$ transmitted through the cell 2. Further, the detecting channel $5c_1$, $5c_2$ and so forth for the respective scattering lights of the detector $5c$ divided radially into a plurality of parts and have shapes which are coaxial with the center of the detector $5c_0$ for the transmitted light. The present embodiment is different from the example shown in FIG. 1 in that the scattered lights $L_{as}$, $L_{bs}$ of the laser lights $L_a$, $L_b$ of two distinct wavelengths are accurately measured by one detector $5c$. Therefore, it is possible to reduce number of detectors $5c$, and the manufacturing cost correspondingly. In another embodiment, it is possible to simplify the construction of the present embodiment by using two light sources $3a$, $3b$ emitting the laser lights $L_a$, $L_b$ of two wavelengths, respectively. In this embodiment, since the scattered lights $L_{as}$, $L_{bs}$ by the laser lights $L_a$, $L_b$ of two wavelengths are detected with using one detector 5c, the respective detectors $5c_0$, $5c_1$, $5c_2$ and so forth, may be arrayed orthogonally to any of the optical axes of the laser lights $L_a$, $L_b$ and the incident angles α of the respective laser lights $L_a$, $L_b$ upon the cell 2 may be identical. In other words, the foregoing light sources 3a, 3b are positioned to be symmetric with respect to the plane 2a normal to the cell 2 and the direction X of the array of the respective detectors $5c_0$, $5c_1$, $5c_2$ and so forth.

Similarly, the light sources 3a, 3b may be positioned when the scattered light does not require detecting with the scattering angles being identical. Further, the number of light sources comprising the light source section of the present embodiment need not be limited to two light sources.

In this embodiment, it is necessary to irradiate the cell 2 with the laser light $L_a$ or $L_b$ of either the light source 3a or 3b. This irradiation may be controlled by adjusting an electric power supplied to the light sources 3a, 3b or by preventing the transmission of the laser light $L_a$ or $L_b$ with the laser shutter.

A described above, the particle size distribution measuring apparatus of the present invention is capable of accurately measuring particle size by using a plurality of wavelengths, thereby eliminating the regions of the particle size having low sensitivity on the whole.

What is claimed is:

1. A particle size distribution measuring apparatus comprising:
   a sample cell for receiving a plurality of particles;
   a light source section for irradiating a first light having a first wavelength onto the sample cell, and for irradiating a second light having a second wavelength onto the sample cell;
   a detector section comprising two or more detectors for measuring the intensity of the first light scattered by one or more particles in the sample cell to generate first light intensity measurements, and for measuring the intensity of the second light scattered by one or more particles in the sample cell to generate second light intensity measurements; and
   a processor for receiving the first light intensity measurements and determining a first low sensitivity region for a particle size, and for receiving the second light intensity measurements and determining a second low sensitivity region for a particle size, wherein the processor determines a particle size distribution by combining the first light intensity measurements and the second light intensity measurements such that the first low sensitivity region and the second low sensitivity region are eliminated in the resulting combined data.

2. The apparatus of claim 1, wherein the light source section comprises a first light source for emitting the first wavelength of light and a second light source for emitting the second wavelength of light.

3. The apparatus of claim 1, wherein the first wavelength is at least 1.5 times larger than the second wavelength.

4. The apparatus of claim 1, wherein the light source section further comprises a plurality of light sources and each light source irradiates light at a plurality of different wavelengths.

5. The apparatus as claim 4, wherein the detector section comprises a plurality of detectors and each detector is configured to measure the intensity of a particular wavelength of light transmitted and scattered by the particles in the sample, wherein the particular wavelength of light is emitted from one of the plurality of light sources.

6. The apparatus of claim 1 where the light source section irradiates laser light at a plurality of wavelengths sequentially.

7. The apparatus of claim 1 further comprising a shutter configured to transmit laser light of a selected wavelength and prevent the transmission of laser light at another wavelength.

8. The apparatus of claim 1 further comprising one or more projection lenses for receiving and condensing the light from the light source section.

9. A method for measuring a particle size distribution of a sample cell having a plurality of particles, the method comprising:
   irradiating, onto the sample cell, a first light having a first wavelength and a second light having a second wavelength;
   detecting the intensity of the first light scattered by one or more particles in the sample cell and generating first light intensity measurements, and detecting the intensity of the second light scattered by one or more particles in the sample cell and generating second light intensity measurements;
   sending the first light intensity measurements and the second light intensity measurements to an arithmetic processing unit;
   generating a first sensitivity curve from the first light intensity measurements to determine a first low sensitivity region for a particle size, and generating a second sensitivity curve from the second light intensity measurements to determine a second low sensitivity region for a particle size; and
   combining the first light intensity measurements with the second light intensity measurements such that the first low sensitivity region and the second low sensitivity region are eliminated in the resulting combined data measurement, thereby providing an accurately determined particle size distribution.

* * * * *